(12) United States Patent
Kersey et al.

(10) Patent No.: US 10,328,230 B2
(45) Date of Patent: Jun. 25, 2019

(54) VAPORIZER

(71) Applicant: Penlon Limited, Abingdon Oxfordshire (GB)

(72) Inventors: Cliff Kersey, Abingdon (GB); James Montgomery, Abingdon (GB); Iain Revell, Abingdon (GB); David Martyn White, Abingdon (GB); Brian Jones, Abingdon (GB)

(73) Assignee: Penlon Limited, Abingdon Oxfordshire (GB)

( * ) Notice: Subject to any disclaimer, the term of this patent is extended or adjusted under 35 U.S.C. 154(b) by 0 days.

(21) Appl. No.: 15/313,620

(22) PCT Filed: May 26, 2015

(86) PCT No.: PCT/EP2015/061606
§ 371 (c)(1),
(2) Date: Nov. 23, 2016

(87) PCT Pub. No.: WO2015/177381
PCT Pub. Date: Nov. 26, 2015

(65) Prior Publication Data
US 2017/0182281 A1 Jun. 29, 2017

(30) Foreign Application Priority Data
May 23, 2014 (GB) .................................. 1409274.6

(51) Int. Cl.
*A61M 16/18* (2006.01)
*A61M 16/10* (2006.01)
(Continued)

(52) U.S. Cl.
CPC .......... *A61M 16/18* (2013.01); *A61M 16/109* (2014.02); *A61M 16/147* (2014.02);
(Continued)

(58) Field of Classification Search
CPC .. A61M 16/18; A61M 16/183; A61M 16/201; A61M 16/109; A61M 2202/0208;
(Continued)

(56) References Cited

U.S. PATENT DOCUMENTS 3,659,601 A * 5/1972 Bushman .............. A61M 16/00
128/203.25
4,881,541 A 11/1989 Eger et al.
(Continued)

FOREIGN PATENT DOCUMENTS

CN 202 277 596 U 6/2012
EP 0945151 A1 9/1999
(Continued)

OTHER PUBLICATIONS

International Search Report and Written Opinion for corresponding Patent Application No. PCT/EP2015/061606 dated Dec. 9, 2015.

*Primary Examiner* — Nicolas A Arnett
(74) *Attorney, Agent, or Firm* — Renner, Otto, Boiselle & Sklar, LLP

(57) ABSTRACT

A vaporizer for delivery of a volatile medium to a gas flow, the vaporizer comprising: a gas delivery unit (3) which receives a flow of gas and provides a flow of gas containing a metered amount of a vaporized medium; a reservoir unit (5) which contains a volatile medium and maintains a supply of the vaporized medium, wherein the reservoir unit is selectively fluidly connected to the gas delivery unit; a gas sensing unit (7) for sensing a flow rate and/or composition of the gas flow; a vaporized medium sensing unit (9) for sensing a flow rate of the vaporized medium; a manifold (10) which includes flow paths for the vaporized medium and fluidly connects the reservoir unit and the vaporized medium sensing unit; and a control unit (11) for controlling a flow (Continued)

rate of the gas flow and an amount of the vaporized medium which is metered into the gas flow.

23 Claims, 14 Drawing Sheets

(51) Int. Cl.
| | |
|---|---|
| A61M 16/14 | (2006.01) |
| A61M 16/16 | (2006.01) |
| G01F 1/68 | (2006.01) |
| G01F 15/00 | (2006.01) |
| G01F 15/14 | (2006.01) |
| G05D 7/06 | (2006.01) |
| A61M 16/20 | (2006.01) |
| G01N 25/18 | (2006.01) |

(52) U.S. Cl.
CPC ........ *A61M 16/161* (2014.02); *A61M 16/183* (2013.01); *A61M 16/201* (2014.02); *G01F 1/68* (2013.01); *G01F 15/002* (2013.01); *G01F 15/005* (2013.01); *G01F 15/14* (2013.01); *G01N 25/18* (2013.01); *G05D 7/0635* (2013.01); *A61M 16/20* (2013.01); *A61M 2016/1035* (2013.01); *A61M 2202/0208* (2013.01); *A61M 2202/0283* (2013.01); *A61M 2202/048* (2013.01); *A61M 2205/3334* (2013.01); *A61M 2205/3368* (2013.01); *A61M 2205/3653* (2013.01)

(58) Field of Classification Search
CPC .... A61M 2202/048; A61M 2202/0283; A61M 2205/3368; A61M 2205/3334; A61M 2016/1035
See application file for complete search history.

(56) References Cited

U.S. PATENT DOCUMENTS

| | | | | | |
|---|---|---|---|---|---|
| 5,049,317 | A | * | 9/1991 | Kiske | A61M 16/104 128/203.14 |
| 5,619,986 | A | * | 4/1997 | Werner | A61M 16/104 128/203.12 |
| 5,649,531 | A | * | 7/1997 | Heinonen | A61M 16/18 128/203.12 |
| 5,832,917 | A | * | 11/1998 | Sarela | A61M 16/18 128/203.12 |
| 6,945,123 | B1 | | 9/2005 | Kuehl et al. | |
| 2010/0269820 | A1 | * | 10/2010 | Danielsen | A61M 16/18 128/202.22 |
| 2011/0186046 | A1 | | 8/2011 | Rindy et al. | |
| 2011/0315139 | A1 | | 12/2011 | Mashak | |
| 2013/0192595 | A1 | | 8/2013 | Tolmie et al. | |
| 2014/0290575 | A1 | * | 10/2014 | Hirose | C23C 16/52 118/696 |
| 2015/0306339 | A1 | * | 10/2015 | Danielsen | A61M 16/18 128/203.14 |

FOREIGN PATENT DOCUMENTS

| | | |
|---|---|---|
| EP | 1044700 A2 | 10/2000 |
| GB | 2400566 A | 10/2004 |
| KR | 2011 0068561 A | 6/2011 |
| WO | WO 2008/151667 A1 | 12/2008 |
| WO | WO 2011/014908 | 2/2011 |

* cited by examiner

VAPORIZER

This application is a national phase of International Application No. PCT/EP2015/061606 filed May 26, 2015 and published in the English language, which claims priority to United Kingdom Patent Application No. 1409274.6 filed May 23, 2014, which are hereby incorporated herein by reference.

The present invention relates to a vaporizer, especially for the delivery of a volatile anaesthetic to a fresh gas flow, and components of such a vaporizer.

Volatile anaesthetics, such as desflurane, are metered into a fresh gas flow which is delivered to a patient for the purpose of achieving general anaesthesia. Other volatile anaesthetics include, for example, halothane, enflurane, isoflurane and sevoflurane.

In one aspect the present invention provides a vaporizer for delivery of a volatile medium to a gas flow, the vaporizer comprising: a gas delivery unit which receives a flow of gas and provides a flow of gas containing a metered amount of a vaporized medium; a reservoir unit which contains a volatile medium and maintains a supply of the vaporized medium, wherein the reservoir unit is selectively fluidly connected to the gas delivery unit; a gas sensing unit for sensing a flow rate and/or composition of the gas flow; a vaporized medium sensing unit for sensing a flow rate of the vaporized medium; a manifold which includes flow paths for the vaporized medium and fluidly connects the reservoir unit and the vaporized medium sensing unit; and a control unit for controlling a flow rate of the gas flow and an amount of the vaporized medium which is metered into the gas flow.

In another aspect the present invention provides a vaporizer for delivery of a volatile medium to a gas flow, the vaporizer comprising: a gas delivery unit which receives a flow of gas and provides a flow of gas containing a metered amount of a vaporized medium; a reservoir unit which contains a volatile medium and maintains a supply of the vaporized medium, wherein the reservoir unit is selectively fluidly connected to the gas delivery unit; and a control unit for controlling a flow rate of the gas flow and an amount of the vaporized medium which is metered into the gas flow; wherein the reservoir unit comprises a tank which contains the volatile medium in liquid form, and a heater which is operative to heat the volatile medium to a vaporization temperature in order to vaporize the volatile medium and maintain an operating pressure in a headspace of the tank, the tank being formed of a thermally-conductive material and providing a thermal mass which is sufficient to maintain the contained volatile medium at the vaporization temperature for at least 3 minutes, optionally for at least 5 minutes, following de-actuation of the heater.

In a further aspect the present invention provides a vaporizer for delivery of a volatile medium to a gas flow, the vaporizer comprising: a gas delivery unit which receives a flow of gas and provides a flow of gas containing a metered amount of a vaporized medium; a reservoir unit which contains a volatile medium and maintains a supply of the vaporized medium, wherein the reservoir unit is selectively fluidly connected to the gas delivery unit; and a control unit for controlling a flow rate of the gas flow and an amount of the vaporized medium which is metered into the gas flow; wherein the reservoir unit comprises a filler assembly by which volatile medium is introduced into the tank, the filler assembly comprising a body which includes a port for receiving a filling container, a chamber which is fluidly connected to the tank, and a valve assembly which, when opened, is operative to open a fluid connection between the port and the chamber so as to provide for filling of the tank with volatile medium from the filling container; wherein the filler assembly comprises a loading/unloading mechanism which is operative to engage the filling container and load/unload the filling container to the valve assembly, the loading/unloading mechanism comprising an engagement member which is adapted to engage the body of the filling container when the filling container is inserted into the port of the body of the filler assembly, and a lever assembly which is coupled to the engagement member and operative between a first, unlocked position and a second, locked position in which the valve assembly is open to allow for filling of the tank by the filling container.

In a still further aspect the present invention provides a vaporizer for delivery of a volatile medium to a gas flow, the vaporizer comprising: a gas delivery unit which receives a flow of gas and provides a flow of gas containing a metered amount of a vaporized medium; a reservoir unit which contains a volatile medium and maintains a supply of the vaporized medium, wherein the reservoir unit is selectively fluidly connected to the gas delivery unit; a gas sensing unit for sensing a flow rate and/or composition of the gas flow; and a control unit for controlling a flow rate of the gas flow and an amount of the vaporized medium which is metered into the gas flow; wherein the gas sensing unit comprises a gas inlet port through which the flow of gas is delivered, an outlet port from which the flow of gas is delivered, a flow path which fluidly connects the gas inlet port and the outlet port, and at least one pair of low rate sensors for sensing the flow rate of the gas flow; wherein the flow rate sensors of each pair of flow rate sensors are physically separated along a length of the flow path, providing an upstream sensor and a downstream sensor, and the upstream sensor includes a temperature sensor element and the downstream sensor includes a heater element and a temperature sensor element, the upstream sensor being configured to sense the ambient temperature of the gas flow and the downstream sensor being configured to determine an energy required to maintain the heater element at a required temperature differential in relation to the ambient temperature as determined by the upstream sensor, whereby the flow rate of the gas flow is determined from an energy required to maintain the heater element at the required temperature differential.

In a yet further aspect the present invention provides a vaporizer for delivery of a volatile medium to a gas flow, the vaporizer comprising: a gas delivery unit which receives a flow of gas and provides a flow of gas containing a metered amount of a vaporized medium; a reservoir unit which contains a volatile medium and maintains a supply of the vaporized medium, wherein the reservoir unit is selectively fluidly connected to the gas delivery unit; a gas sensing unit for sensing a flow rate and/or composition of the gas flow; and a control unit for controlling a flow rate of the gas flow and an amount of the vaporized medium which is metered into the gas flow; wherein the gas sensing unit comprises a gas inlet port through which the flow of gas is delivered, an outlet port from which the flow of gas is delivered, a flow path which fluidly connects the gas inlet port and the outlet port, and at least one flow rate sensor for sensing the flow rate of the gas flow; wherein the flow path includes a stub path, and the gas sensing unit further comprises at least one gas characteristic sensor in the stub path for measuring a characteristic of the gas flow which is representative of a composition of the gas flow, with the measurement from the at least one gas characteristic sensor being used to provide a compensation factor for the flow rate of the gas flow as measured by the at least one flow rate sensor.

In a still yet further aspect the present invention provides a vaporizer for delivery of a volatile medium to a gas flow, the vaporizer comprising: a gas delivery unit which receives a flow of gas and provides a flow of gas containing a metered amount of a vaporized medium; a reservoir unit which contains a volatile medium and maintains a supply of the vaporized medium, wherein the reservoir unit is selectively fluidly connected to the gas delivery unit; a gas sensing unit for sensing a flow rate and/or composition of the gas flow; a vaporized medium sensing unit for sensing a flow rate of the vaporized medium; and a control unit for controlling a flow rate of the gas flow and an amount of the vaporized medium which is metered into the gas flow; wherein the vaporized medium sensing unit comprises a body which is thermally connected to the reservoir unit and includes a flow channel which includes an inlet port which is fluidly connected to the reservoir unit and an outlet port which is fluidly connected to the gas delivery unit, and at least one flow sensor for detecting a flow rate of the vaporized medium through the flow channel.

Preferred embodiments of the present invention will now be described hereinbelow by way of example only with reference to the accompanying drawings, in which.

Figure 1:
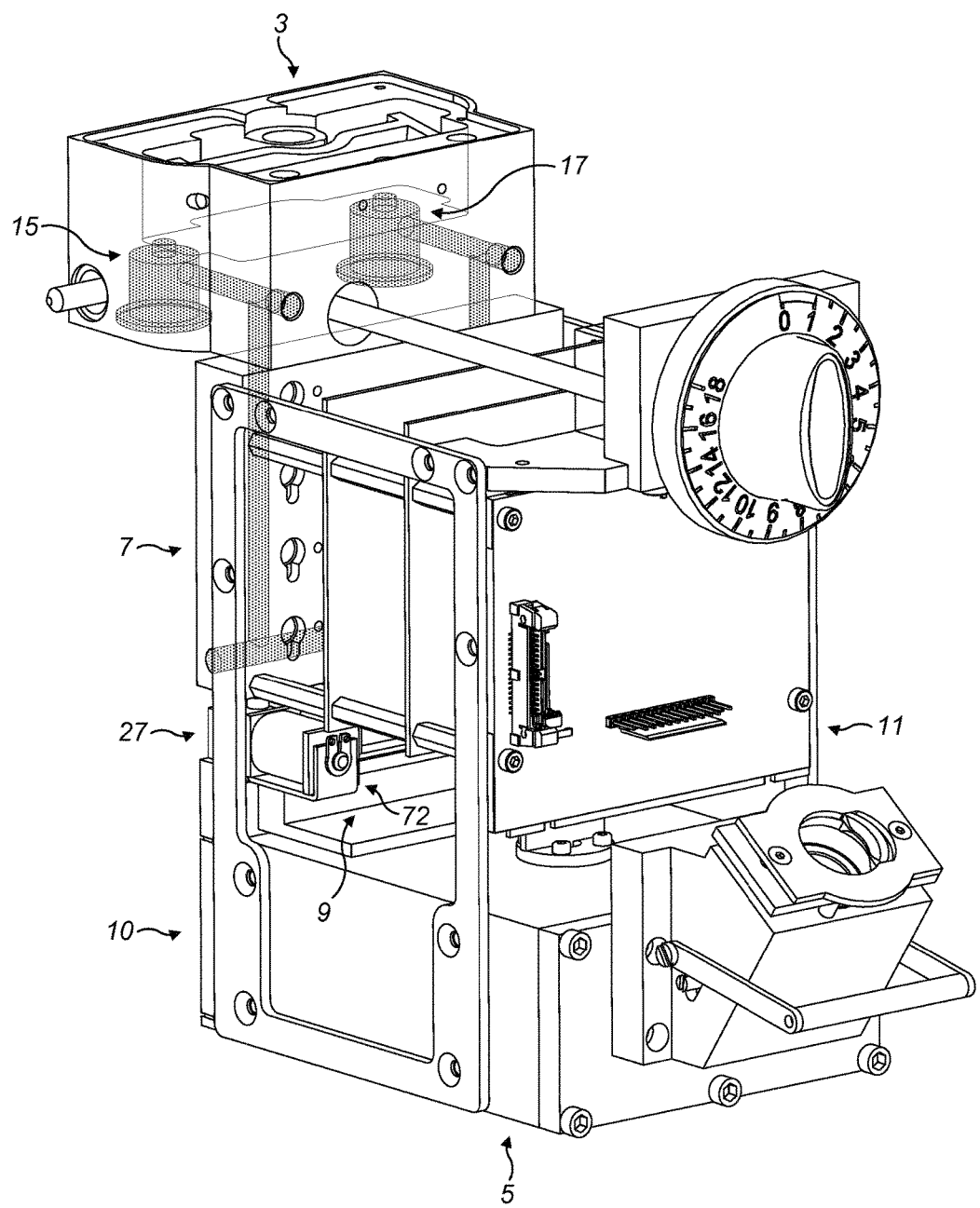
FIG. 1 illustrates a front perspective view of a vaporizer in accordance with one embodiment of the present invention.
Figure 2:
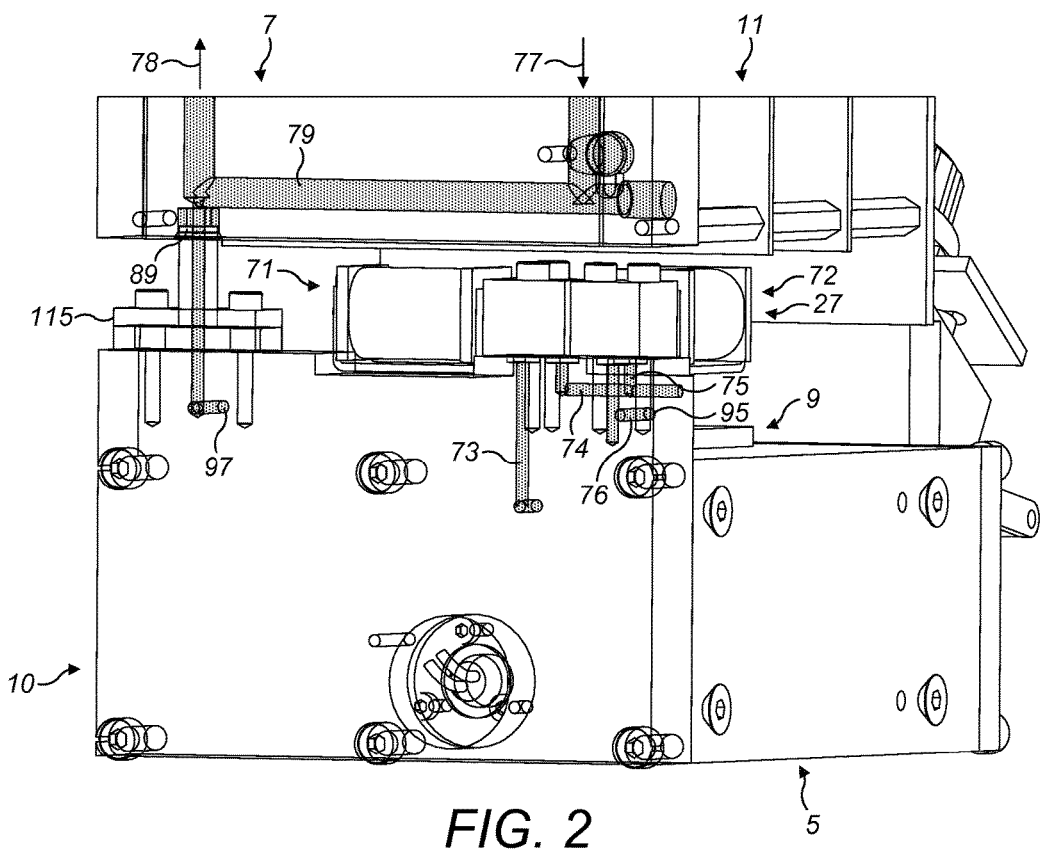
FIG. 2 illustrates a rear perspective view of the vaporizer of FIG. 1.
Figure 5A:
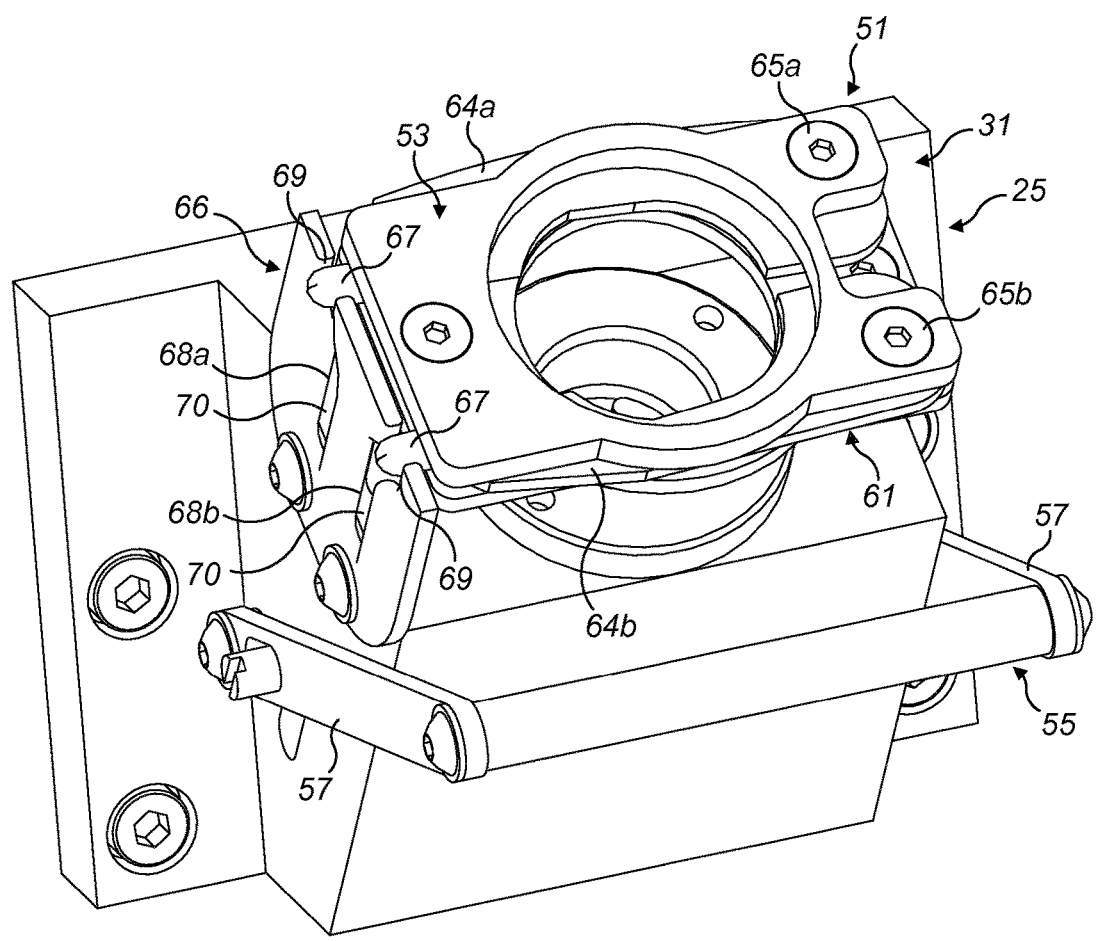
Figure 6A:
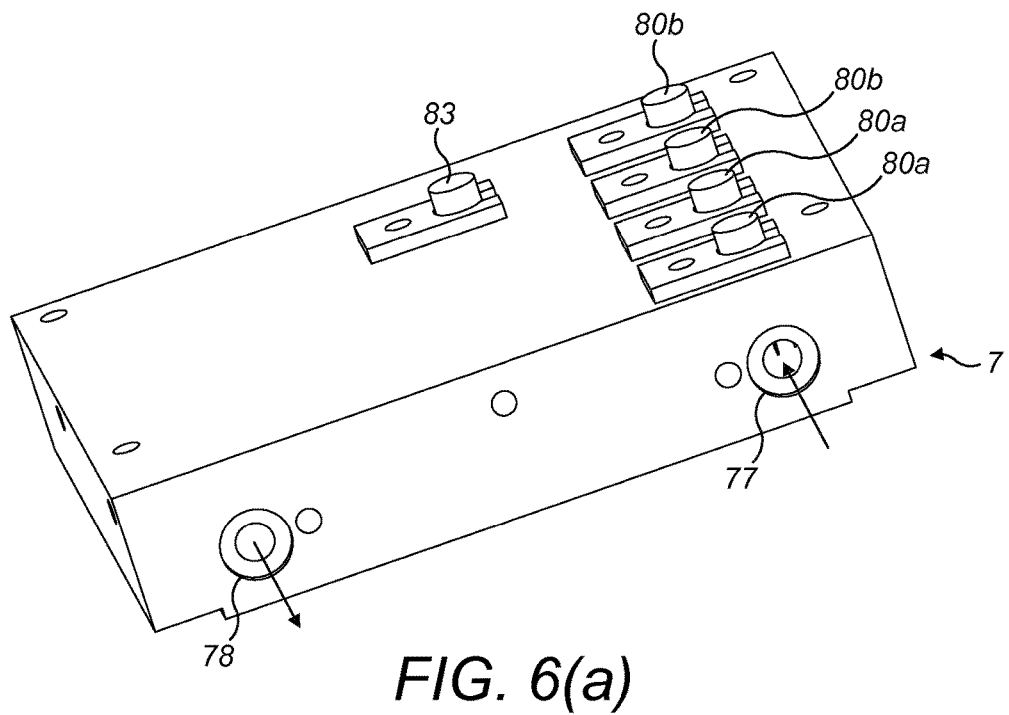
Figure 6B:
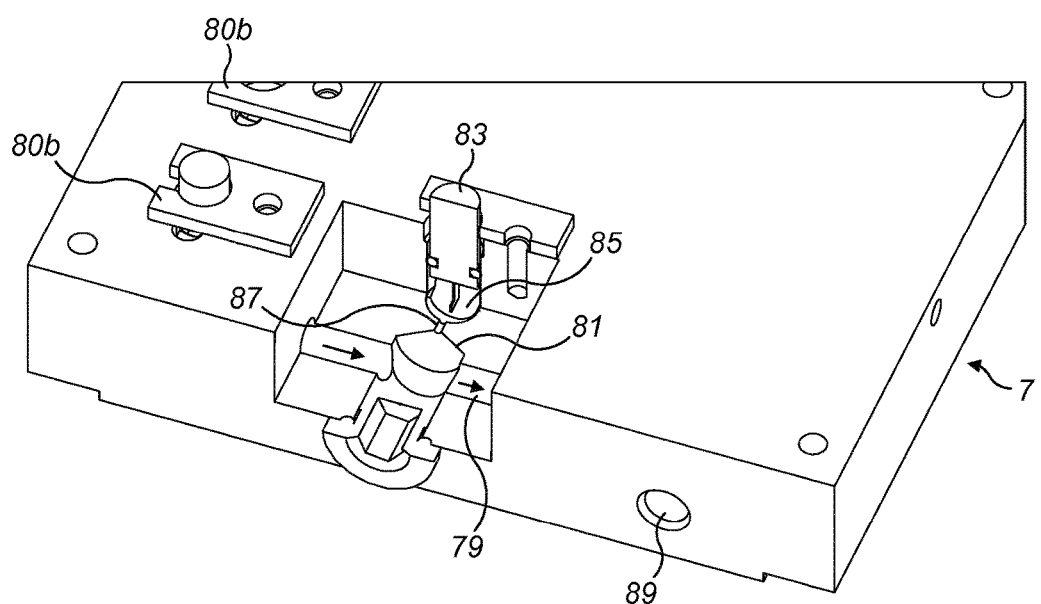
Figure 7:
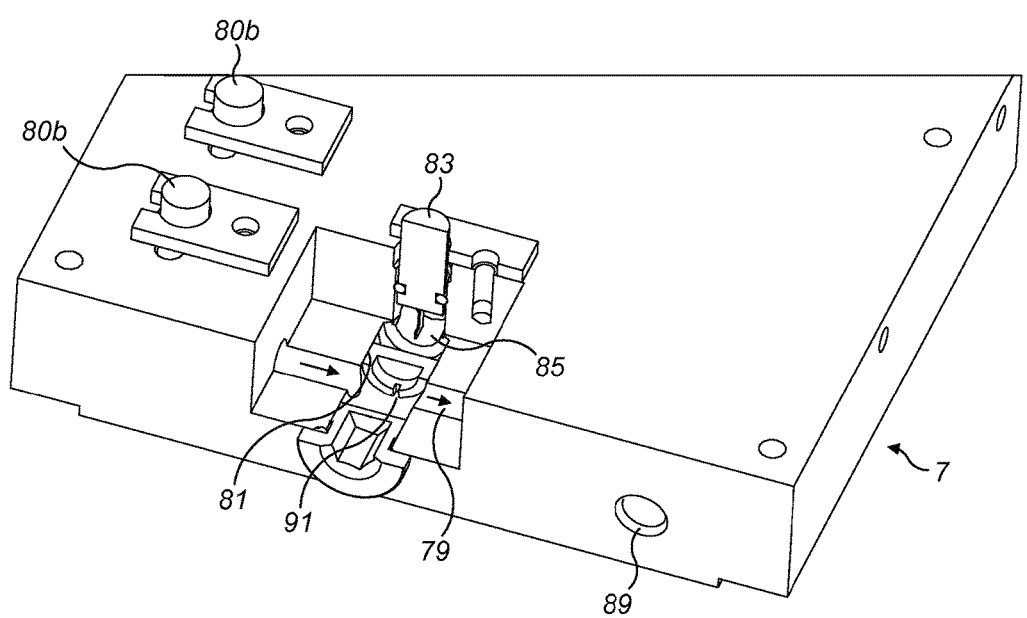
Figure 8A:
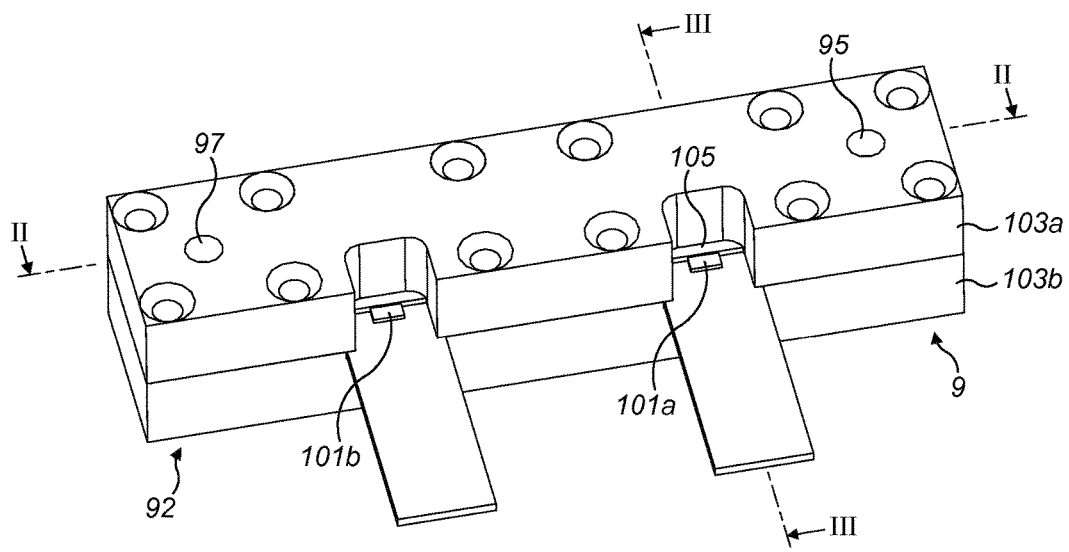
Figure 8B:
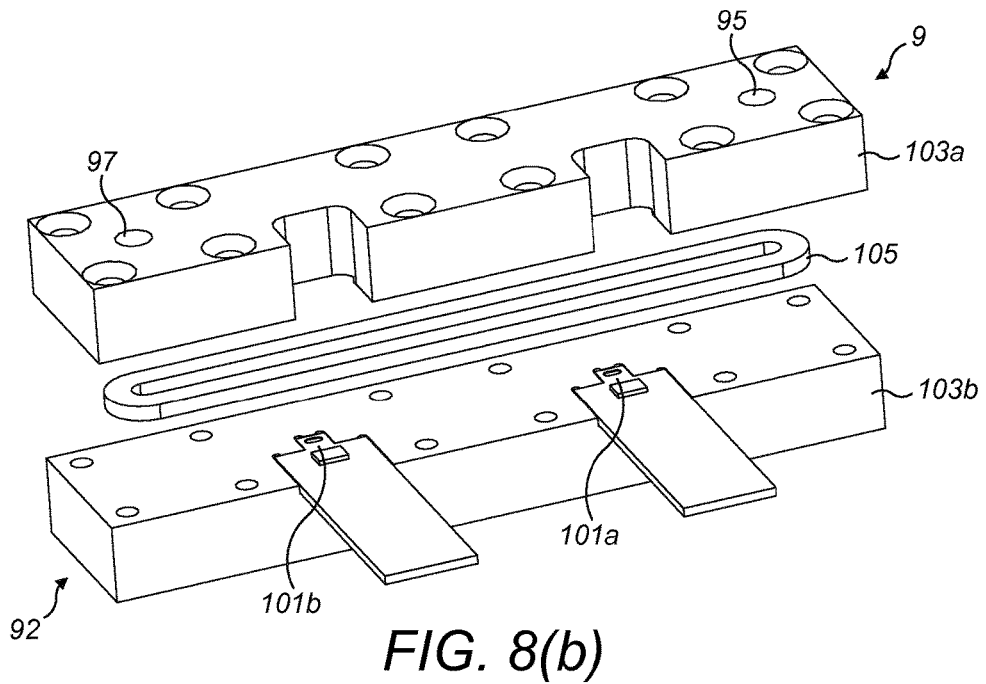
Figure 8C:
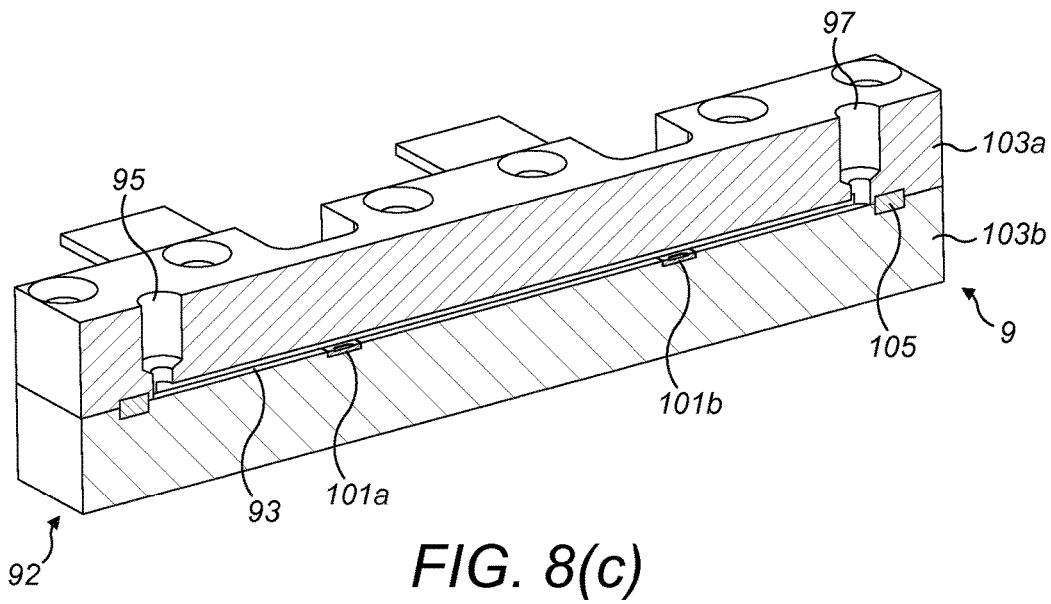
Figure 8D:
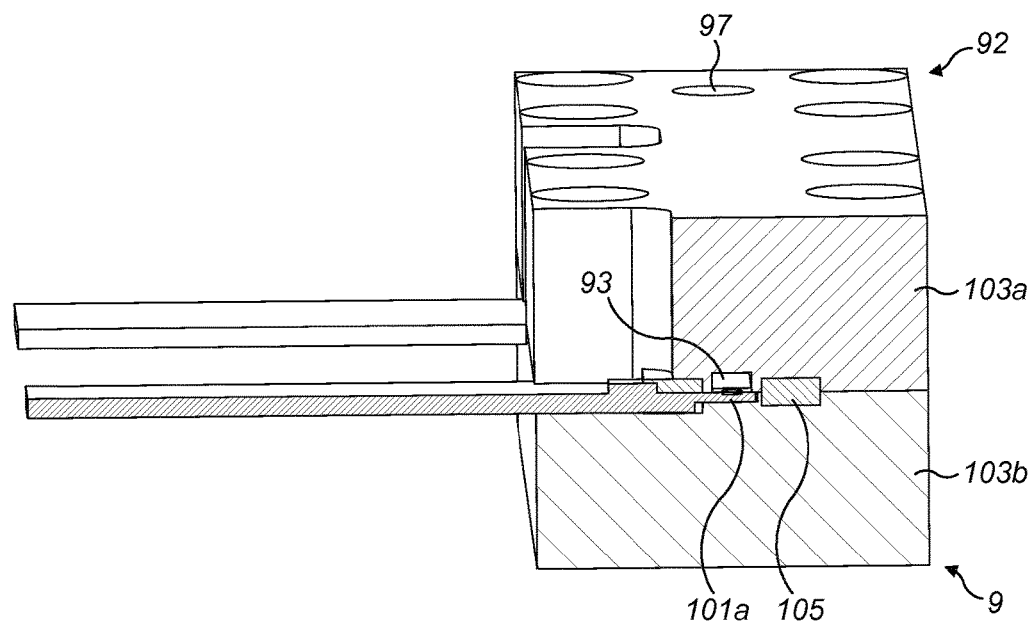

FIGS. 5(a) and (b) illustrate perspective views of a modified filler assembly for the vaporizer of FIG. 1;

FIG. 6(a) illustrates a perspective view of the fresh gas sensing unit of the vaporizer of FIG. 1;

FIG. 6(b) illustrates a part cut-away fragmentary perspective view of the fresh gas sensing unit of FIG. 6(a);

FIG. 7 illustrates a part cut-away fragmentary perspective view of a modified fresh gas sensing unit for the vaporizer of FIG. 1;

FIG. 8(a) illustrates a perspective view of the vaporized medium flow sensor of the vaporizer of FIG. 1;

FIG. 8(b) illustrates an exploded perspective view of the vaporized medium flow sensor of FIG. 8(a);

FIG. 8(c) illustrates a first vertical sectional view (along section II-II in FIG. 8(a)) through the vaporized medium flow sensor of FIG. 8(a); and FIG. 8(d) illustrates a second vertical sectional view (along section III-III in FIG. 8(a)) through the vaporized medium flow sensor of FIG. 8(a).

The vaporizer comprises a fresh gas delivery unit 3 which receives a flow of fresh gas and provides a flow of fresh gas containing a metered amount of a vaporized medium, a reservoir unit 5 which contains a volatile medium and maintains a supply of the vaporized medium, a fresh gas sensing unit 7 for sensing a flow rate and composition of the fresh gas, a vaporized medium sensing unit 9 for sensing a flow rate of the vaporized medium, a manifold 10 which includes flow paths for the vaporized medium, and a control unit 11 for controlling the flow rate of the fresh gas flow and the amount of the vaporized medium which is metered into the fresh gas flow.

The fresh gas delivery unit 3 comprises an inlet 15 which is connected to a supply of fresh gas and an outlet 17 which provides a flow of fresh gas containing a metered amount of a vaporized medium.

In this embodiment the fresh gas comprises a mixture of oxygen, air and nitrous oxide, but can have any desired form.

Figure 3A:
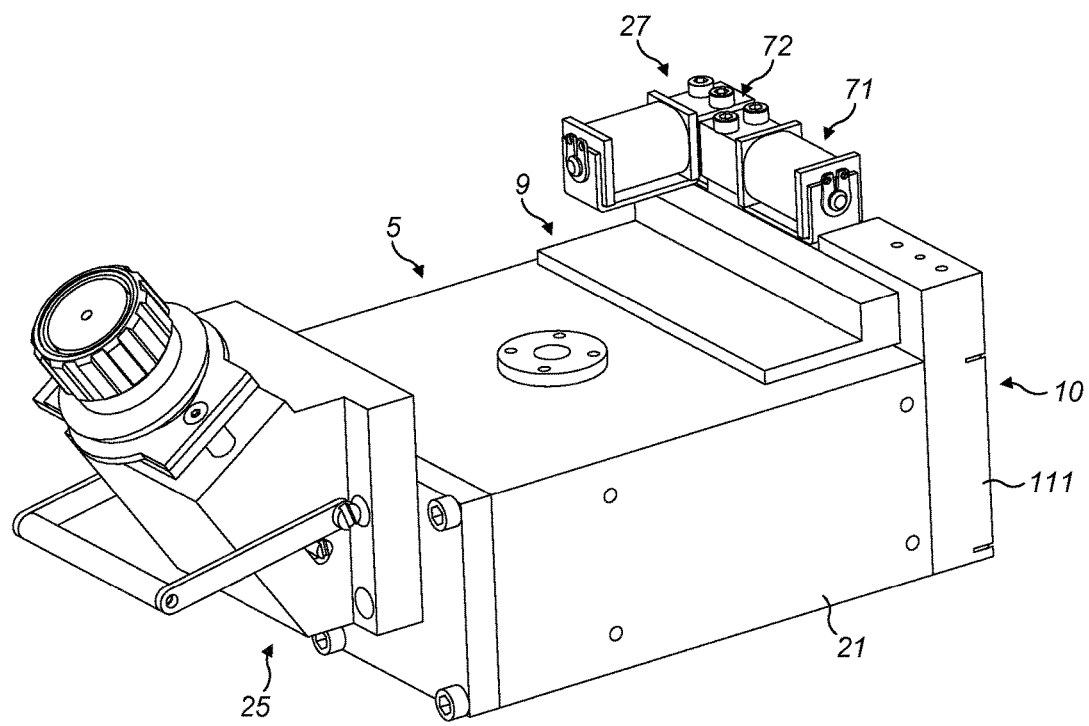
FIG. 3(a) illustrates a front perspective view of the reservoir unit of the vaporizer of FIG. 1.
Figure 3B:
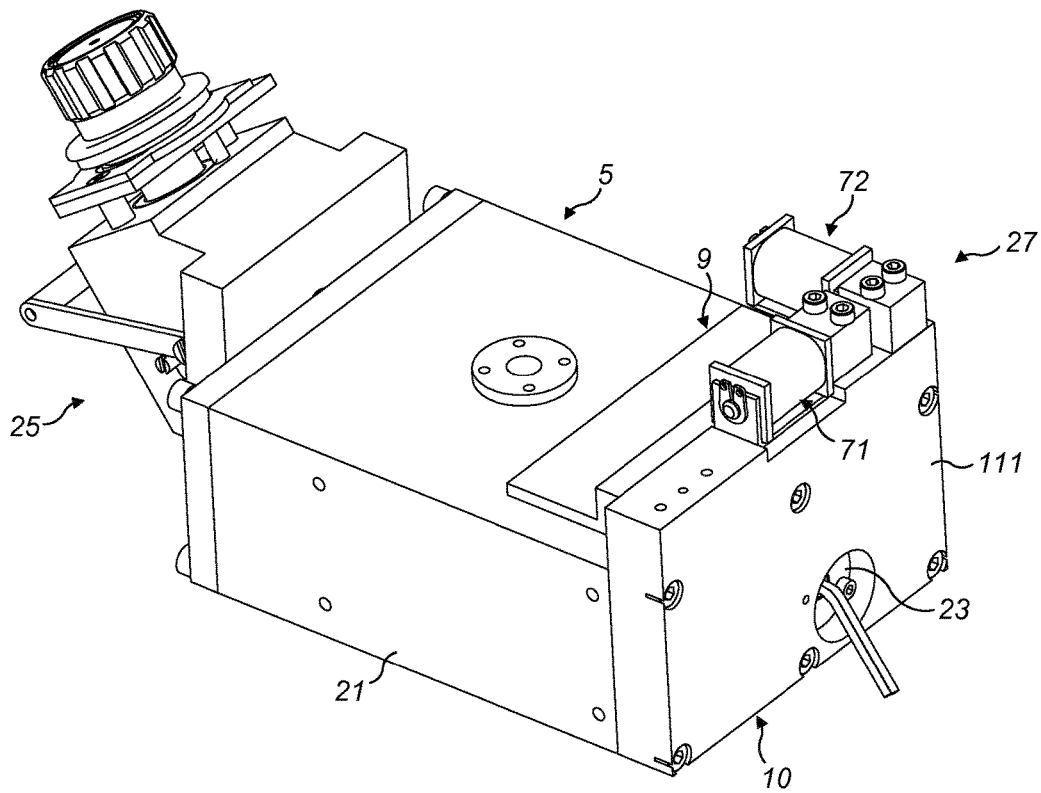
FIG. 3(b) illustrates a rear perspective view of the reservoir unit of FIG. 3(a)
Figure 3C:
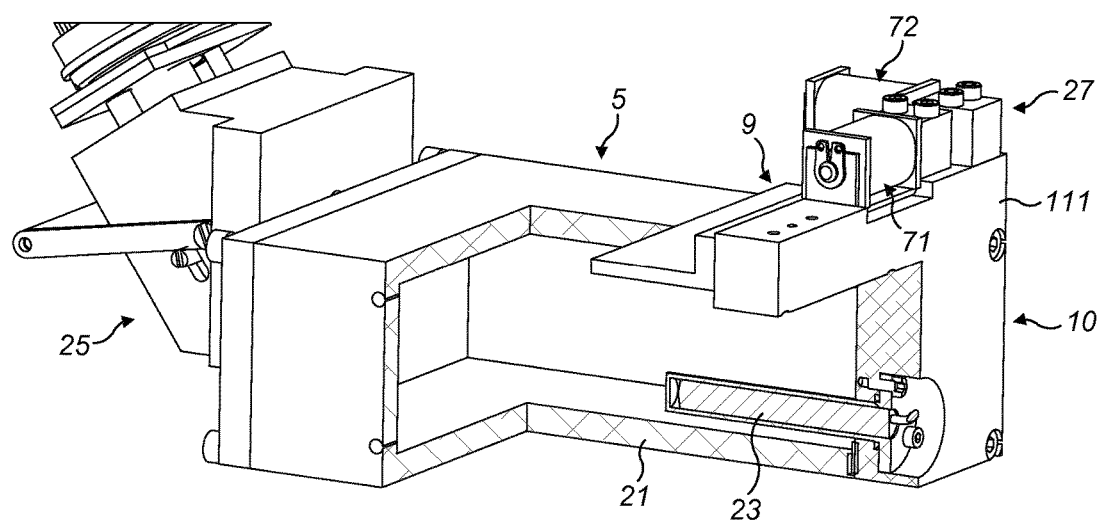
FIG. 3(c) illustrates a part cut-away perspective view of the reservoir unit of FIG. 3(a)
Figure 4A:
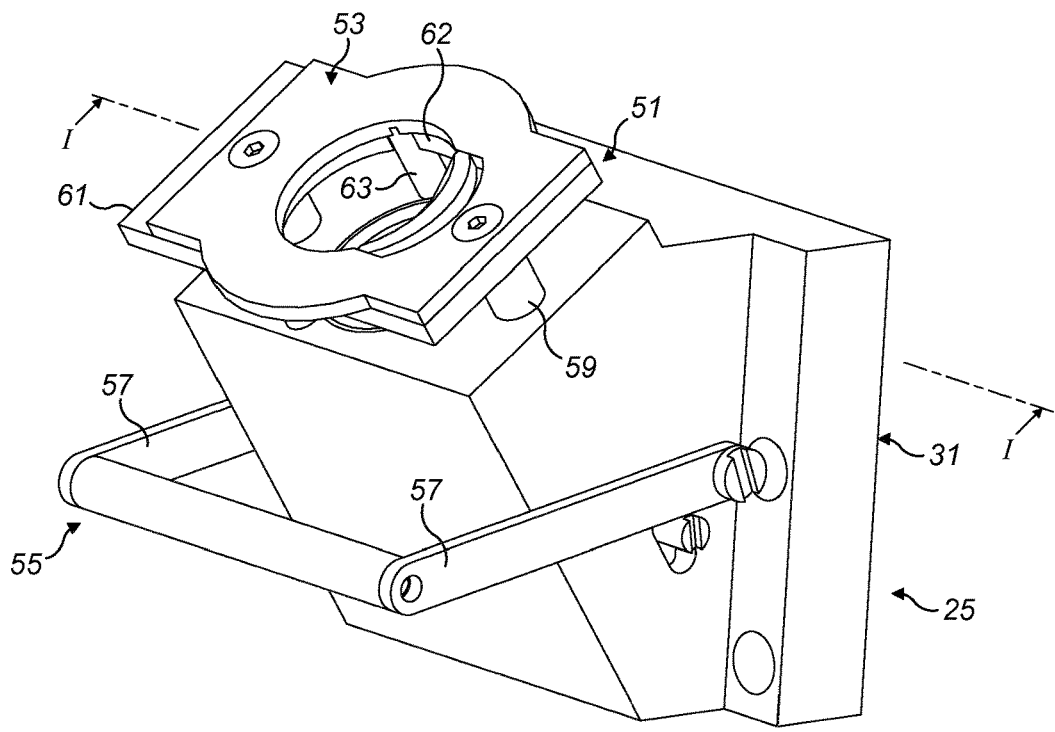
FIG. 4(a) illustrates a first front perspective view of the filler assembly of the reservoir unit of FIG. 3(a)
Figure 4B:
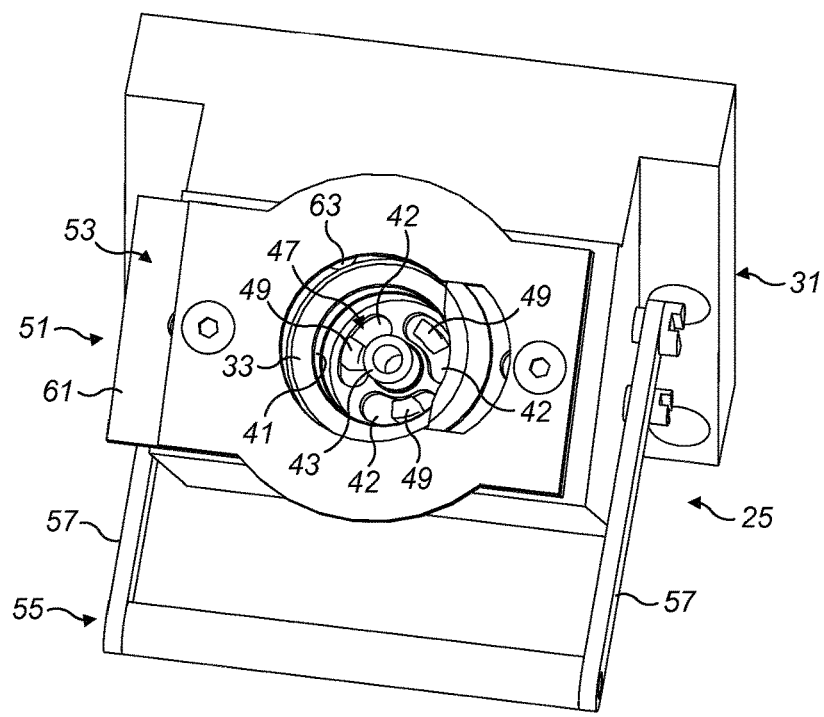
FIG. 4(b) illustrates a second front perspective view of the filler assembly of FIG. 4(a)
Figure 4C:
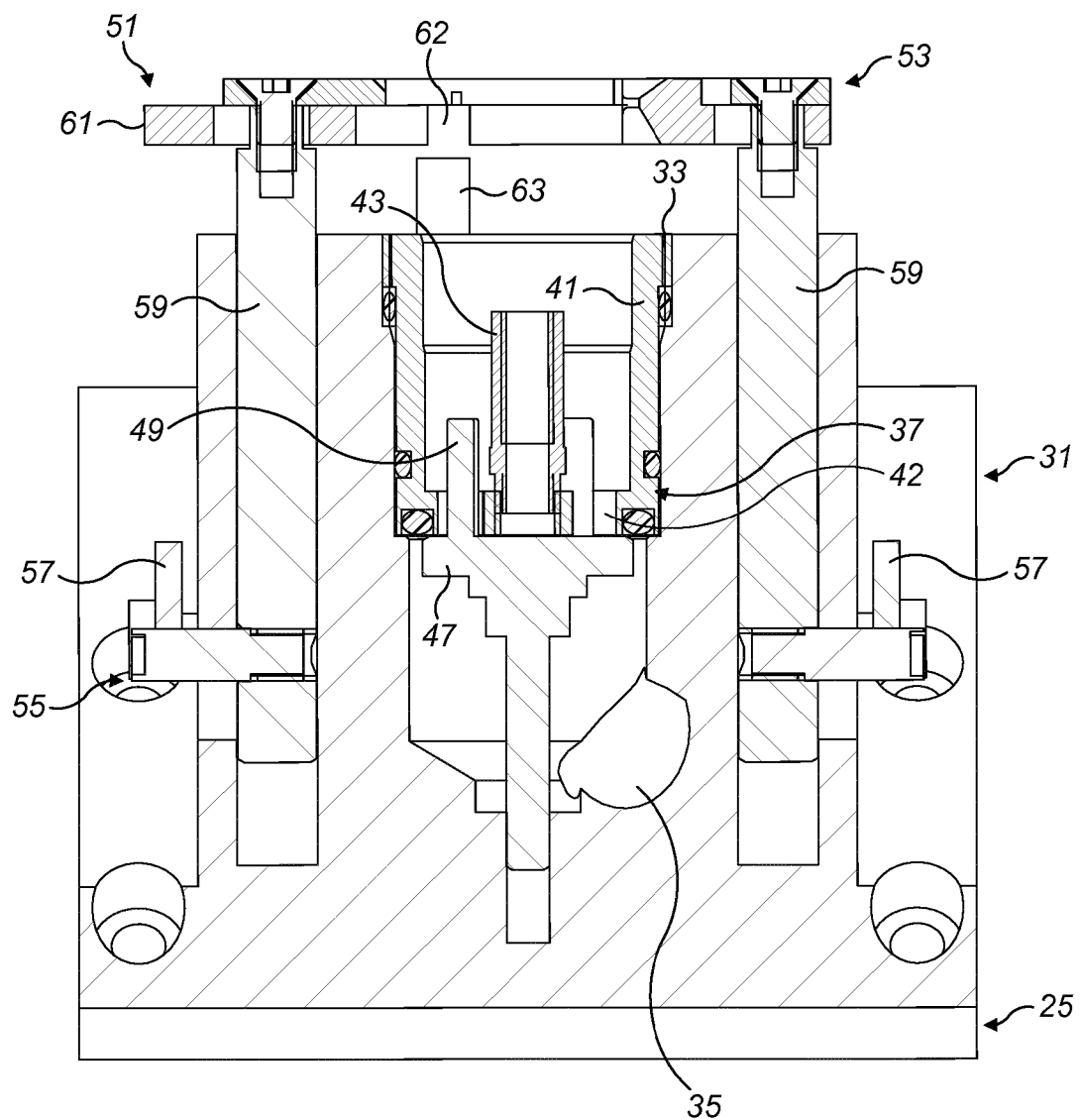
FIG. 4(c) illustrates a sectional view (along section I-I in FIG. 4(a)) of the filler assembly of FIG. 4(a)
Figure 4D:
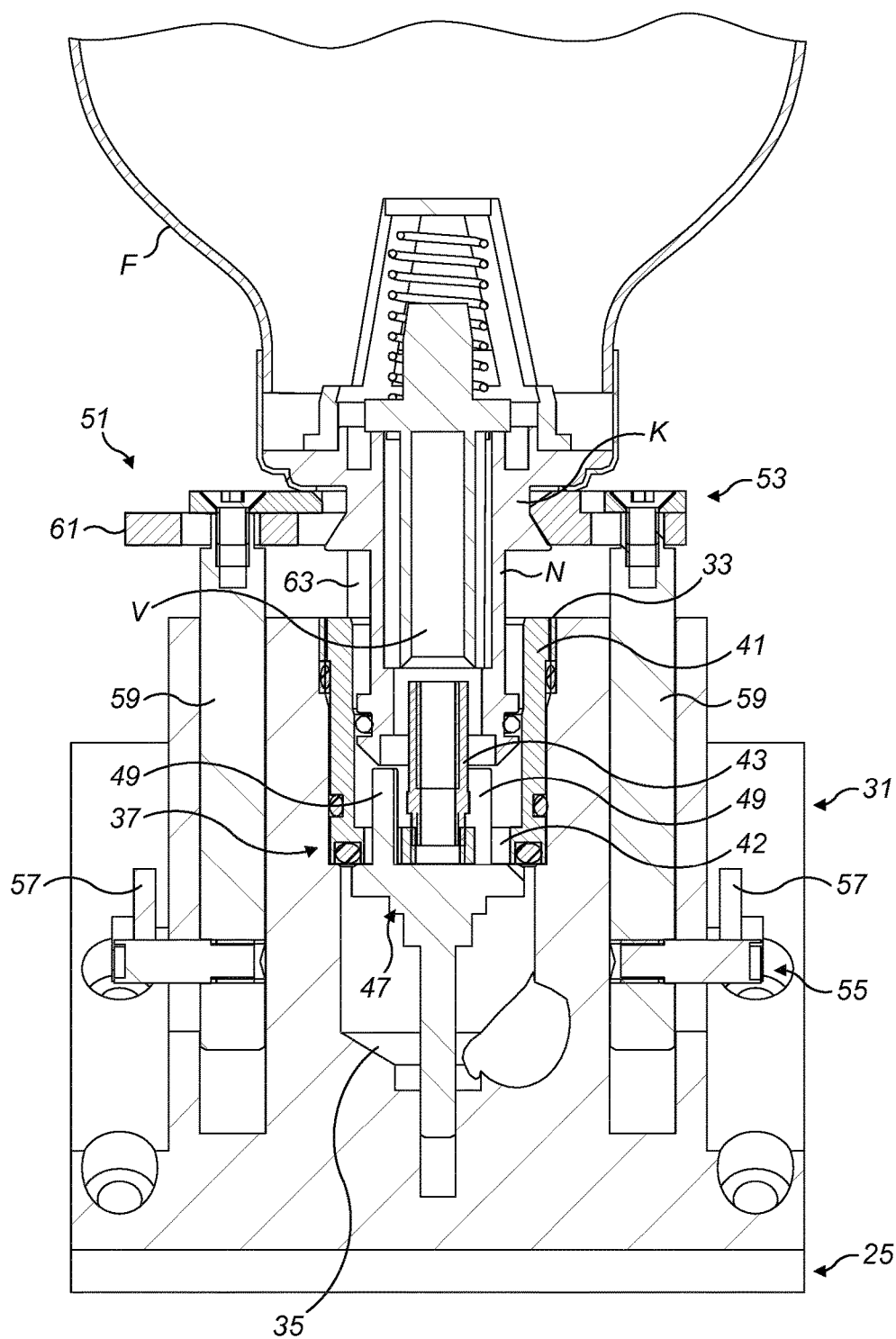
FIG. 4(d) illustrates a sectional view (along section I-I in FIG. 4(a)) of the filler assembly of FIG. 4(a), with a filling container fitted thereto in a first, rest position.
Figure 4E:
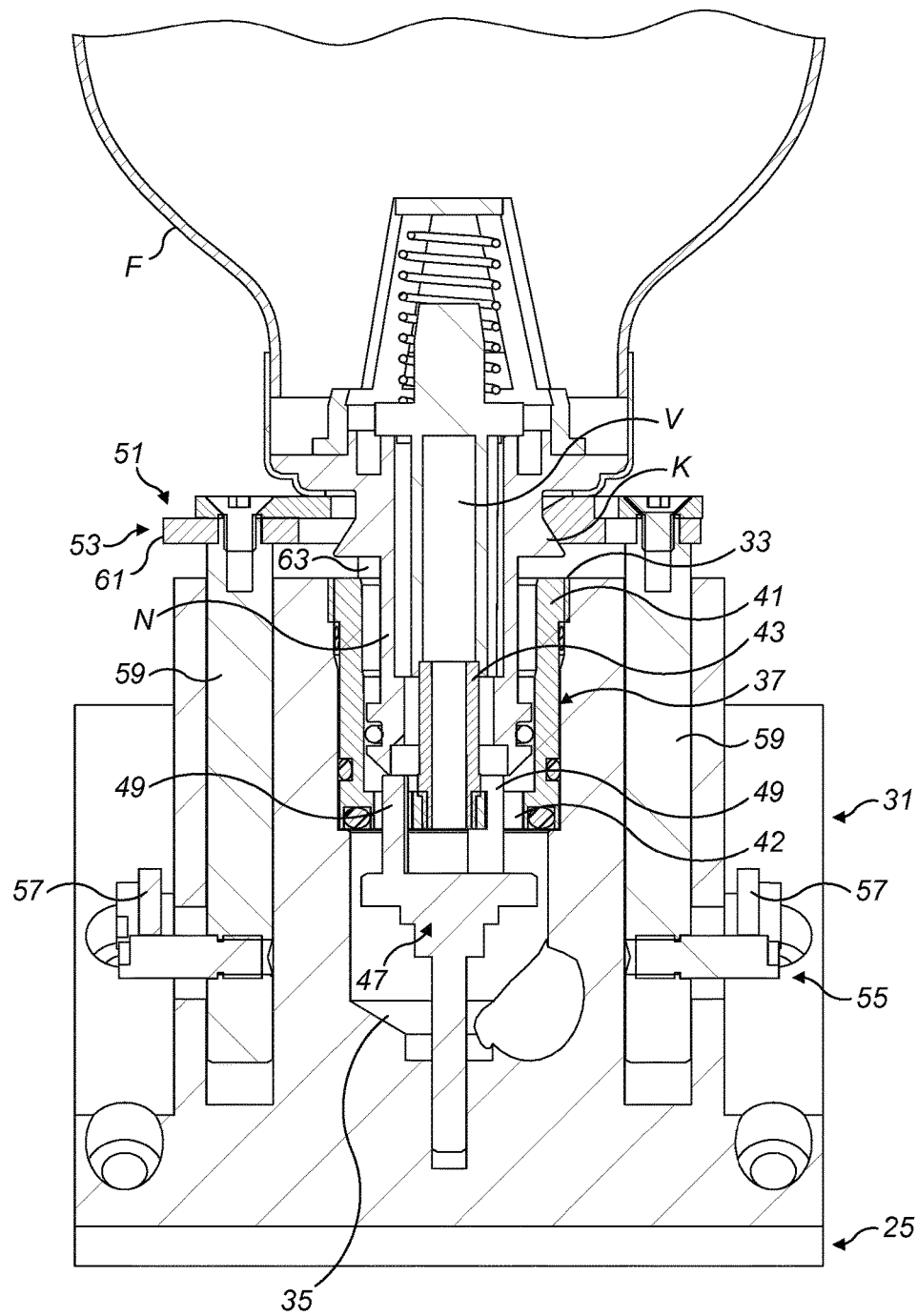
FIG. 4(e) illustrates a sectional view (along section I-I in FIG. 4(a)) of the filler assembly of FIG. 4(a), with a filling container fitted thereto in a second, filling position.

As particularly illustrated in FIGS. 3(a) to (c), the reservoir unit 5 comprises a tank 21 which contains the volatile medium in liquid form, a heater 23 which is operative to heat the volatile medium to a vaporization temperature in order to vaporize the volatile medium and maintain an operating pressure in a headspace of the tank 21, a filler assembly 25 by which volatile medium is introduced into the tank 21, and a valve assembly 27 by which the vaporized medium which is delivered to the fresh gas flow can be metered and shut off.

In this embodiment the tank 21 is formed of a thermally-conductive material and, together with the manifold 10, is of sufficient thermal capacity in order maintain the contained volatile medium at the vaporization temperature for a pre-determined period of time, in this embodiment at least 3 minutes and preferably at least 5 minutes, following de-actuation of the heater 23. With this configuration, by providing the tank 21 with a thermal store, the vaporizer can continue to vaporize the volatile medium without provision of power to the heater 23, either from mains or battery, and optionally is configured to enable a vaporized medium delivery rate of at least 1.2 L/min for the predetermined period of time. In existing systems, power is typically maintained to the heater 23 by use of a battery.

In this embodiment the tank 21 is defined in part by the manifold 10.

In this embodiment the tank 21 is formed of aluminum, which is highly-thermally conductive. In preferred embodiments the tank 21 could be formed of any material which is compatible with the volatile medium and has a thermal conductivity of at least about 100 W/(m.K), optionally at least about 150 W/(m.K), optionally at least about 200 W/(m.K). In an alternative embodiment the tank 21 or at least parts thereof could be formed of brass.

In this embodiment, as particularly illustrated in FIGS. 4(a) to (e), the filler assembly 25 comprises a body 31 which includes a port 33 for receiving a filling container F, here a bottle, a chamber 35 which is fluidly connected to the tank 21, and a valve assembly 37 which, when opened, is operative to open a fluid connection between the port 33 and the chamber 35 so as to provide for filling of the tank 21 with volatile medium from the filling container F.

In this embodiment the valve assembly 37 comprises a bore 41 which sealingly receives an external nozzle N of the filling container F and includes at least one valve opening 42 at one, distal end thereof, a seat 43 which receives a valve element V of the filling container F, which is internal to the nozzle N and when depressed opens a fluid connection between the nozzle N and a body of the filling container F, and a valve element 47 which is normally biased to close the at least one valve opening 42 and is engaged by the nozzle N of the filling container F to displace the valve element 47 and open the at least one valve opening 42.

In this embodiment the valve element 47 includes at least one, here a plurality of projections 49 which project through the at least one valve opening 42, and are engaged by the nozzle N of the filling container F to displace the valve element 47.

In this embodiment the seat 43 extends proximally of the projections 49 of the valve element 47. With this configuration, inadvertent operation of the valve element 47 by introduction of, for example, a finger into the bore 41, is prevented.

The filler assembly 25 further comprises a loading/unloading mechanism 51 which is operative to engage the filling container F and load/unload the filling container F to the valve assembly 37.

In this embodiment the loading/unloading mechanism 51 comprises an engagement member 53 which is adapted to engage a body of the filling container F, in this embodiment the neck K of the filling container F, when the filling container F is inserted into the port 33 of the body 31 of the filler assembly 25, and a lever assembly 55 which is coupled to the engagement member 53 and is operative between a first, unlocked position (as illustrated in FIG. 4(*d*)) and a second, locked position (as illustrated in FIG. 4(*e*)) in which the valve assembly 37 is open to allow for filling of the tank 21 by the filling container F.

In this embodiment the lever assembly 55 comprises a lever 57, here comprising first and second arms, which is pivotally coupled to the body 31 of the filler assembly 25, and a coupling 59, here comprising first and second rods, which couples the lever 57 to the engagement member 53.

In operation, the nozzle N of the filling container F is inserted into the bore 41 of the valve assembly 37, with the lever assembly 55 in the first, unlocked position, and, on moving the lever 57 to the second, locked position, the engagement member 53 is moved in relation to the body 31 of the filler assembly 25, which causes the valve element V of the filling container F to engage the seat 43 of the valve assembly 37 and the nozzle N of the filling container F to engage the valve element 47 of the valve assembly 37, which causes the valve element V of the filling container F and the valve element 47 of the valve assembly 37 to be opened. In this embodiment the nozzle N of the filling container F engages the valve element 47 of the valve assembly 37 ahead of the valve element V of the filling container F engaging the seat 43 of the valve assembly 37, such that the valve element 47 of the filler assembly 25 is opened ahead of the valve element V of the filling container F.

In this embodiment the engagement member 53 includes a slide element 61 which is movable laterally and acts to engage the body of the filling container F, here the neck K of the filling container F, such as to fix the filling container F to the engagement member 53.

In this embodiment the slide element 61 includes a recess 62, which, when the engagement member 53 is moved to the locked position, is located at a detent 63, here a projection, in order to prevent sliding of the slide element 61 and inadvertent release of the filling container F from the engagement member 53 during a filling operation. In an alternative embodiment the recess 62 could instead be a projection.

In one embodiment the recess 62 and the detent 63 can be configured such that the slide element 61 is moved to an open position when the lever assembly 55 is moved to the unlocked position.

In an alternative embodiment the lever assembly 55 could be configured such as to be movable from the unlocked position to a release position by movement of the lever 57 is a sense opposite to that in which the lever 57 is moved to the locked position, and the recess 62 and the detent 63 can be configured such that the slide element 61 is moved to an open position when the lever assembly 55 is in the release position.

In this embodiment the filler assembly 25 is thermally connected to the tank 21.

Figure 5B:
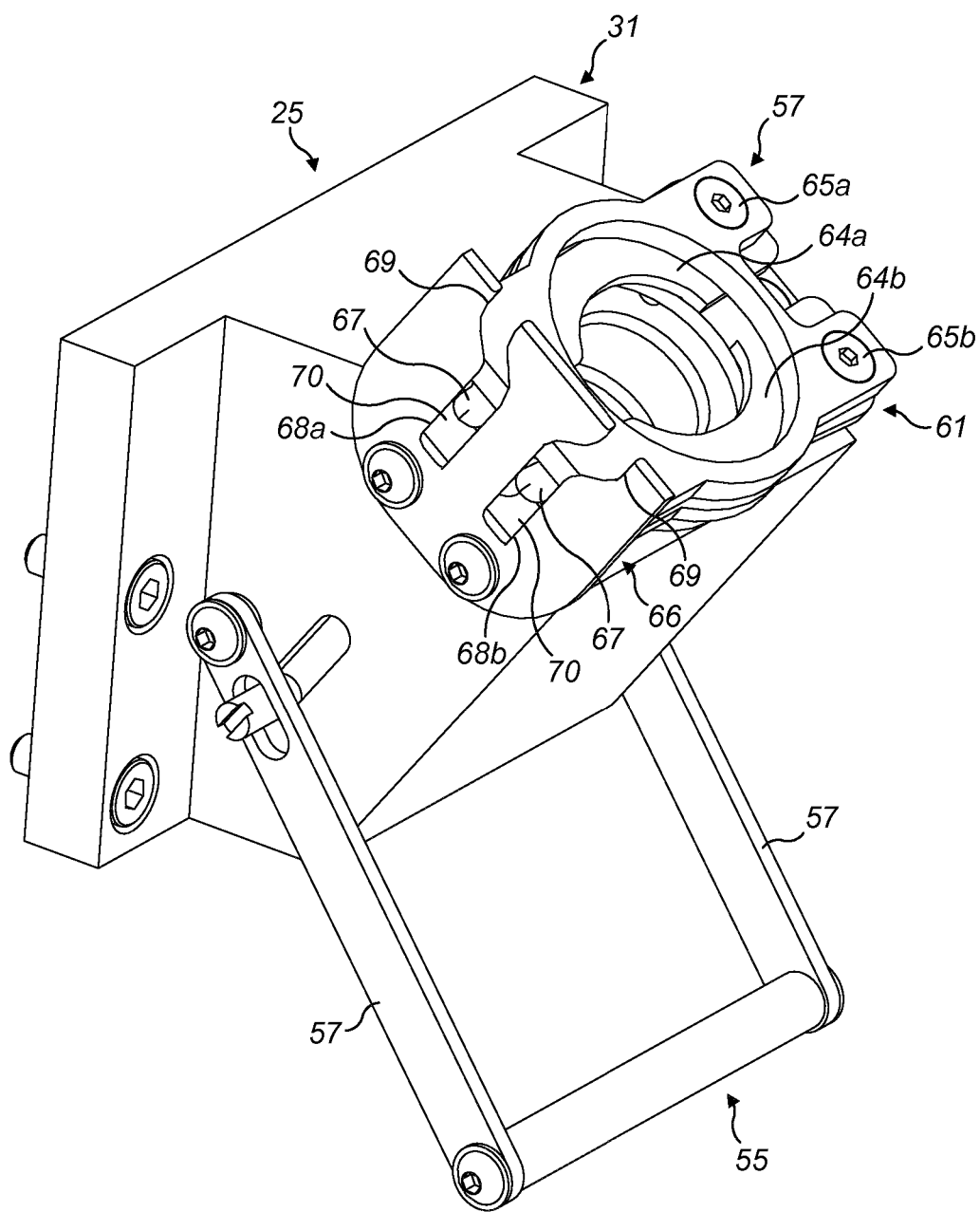

FIGS. 5(*a*) and (*b*) illustrate a modification to the filler assembly 25 of FIGS. 4(*a*) to (*e*).

In this embodiment the slide element 61 comprises at least one slide part 64 which is slideably rotated about at least one pivot 65, here comprising first and second slide parts 64*a*, *b* which are rotated about first and second pivots 65*a*, *b*, and the loading/unloading mechanism 51 further comprises a guide member 66 which acts to cause the slide parts 64*a*, *b* to slide laterally when the loading/unloading mechanism 51 is moved axially between the unlocked (as illustrated in FIG. 5(*a*)) and locked (as illustrated in FIG. 5(*b*)) positions.

In this embodiment each slide part 64*a*, *b* includes a projection 67, here at a distal end to the pivot 65*a*, *b*, and the guide member 66 includes at least one guide 68, here first and second guides 68*a*, *b*, which receive the projections 67 of the respective slide parts 64*a*, *b*.

In this embodiment the guides 68*a*, *b* include a first guide section 69, in which the projections 67 are located when the loading/unloading mechanism 51 is in the unlocked position, and a second guide section 70 which is disposed laterally inwardly of the first guide section 69, in which the projections 67 are located when the loading/unloading mechanism 51 is in the locked position.

With this configuration, when the loading/unloading mechanism 51 is in the unlocked position, the projections 67 of the slide parts 64*a*, *b* are located in the first guide sections 69 of the guides 68*a*, *b* and the slide parts 64*a*, *b* have a first, laterally-outward position which allows the neck K of the filling container F to be inserted into the bore 41 of the valve assembly 37, and, when the loading/unloading mechanism 51 is moved to the locked position, in this embodiment by axial displacement of the engagement member 53, the projections 67 of the slide parts 64*a*, *b* are located in the second guide sections 70 of the guides 68*a*, *b* and the slide parts 64*a*, *b* have a second, laterally-inward position in which the neck K of the filling container F is engaged by the slide parts 64*a*, *b* and prevents release of the filling container F during a filling operation. When the loading/unloading mechanism 51 is returned to the unlocked position, the projections 67 of the slide parts 64*a*, *b* are returned to the first guide sections 69 of the guides 68*a*, *b* and the slide parts 64*a*, *b* have the first, laterally-outward position which allows the neck K of the filling container F to be removed from the bore 41 of the valve assembly 37.

In this embodiment the guides 68*a*, *b* each have the form of a track, here formed by a through slot.

In this embodiment the valve assembly 27 comprises a shut-off valve 71 which is operated as required to prevent delivery of the vaporized medium into the fresh gas flow, and a metering valve 72 which regulates the amount of the vaporized medium which is metered into the fresh gas flow in accordance the measured flow rate of the fresh gas flow, as will be described in more detail hereinbelow.

In this embodiment the shut-off valve 71 includes an inlet port 73 which is fluidly connected to the tank 21 of the reservoir unit 5 through a flow path in the manifold 10, and an outlet port 74 which is fluidly connected to an inlet port 75 of the metering valve 72 through a flow path in the manifold 10.

In this embodiment the metering valve 72 includes an inlet port 75 which is fluidly connected to the outlet port 74 of the shut-off valve 72 through a flow path in the manifold 10, and an outlet port 76 which is fluidly connected to the vaporized medium sensing unit 9 through a flow path in the manifold 10.

In this embodiment, as particularly illustrated in FIGS. 6(a) and (b), the fresh gas sensing unit 7 comprises a fresh gas inlet port 77 through which the flow of fresh gas is delivered, an outlet port 78 from which the flow of fresh gas is delivered, a flow path 79 which fluidly connects the fresh gas inlet port 77 and the outlet port 78, and at least one flow rate sensor 80 for sensing the flow rate of the fresh gas flow.

In this embodiment the flow path 79 has a diameter of 5 mm.

In this embodiment the fresh gas sensing unit 7 comprises at least one pair of flow rate sensors 80, here first and second pairs of flow rate sensors 80a, 80b.

In this embodiment the flow rate sensors 80a, 80b are mass flow rate sensors, here mass flow sensors, which comprise a heater element and a temperature sensor element.

By providing a pair of flow rate sensors 80, each physically separated along a length of the flow path, the fresh gas sensing unit 7 can provide a more accurate measurement. The present inventors have determined that a more accurate measurement can be obtained by configuring the pair of flow rate sensors 80 such as to utilize the heater and temperature sensor elements of the downstream sensor 80 and only the temperature sensor element of the upstream sensor 80 in performing a flow rate measurement.

In this embodiment the upstream sensor 80 is configured to sense the ambient temperature of the fresh gas flow and the downstream sensor 80 is configured to determine the energy required to maintain the heater element at a required temperature differential in relation to the ambient temperature as determined by the upstream sensor 80, which energy determines the flow rate of the fresh gas flow. In this embodiment the downstream sensor 80 heats the fresh gas flow to a predetermined temperature differential in relation to, here 30° C. above, the ambient temperature as determined by the upstream sensor 80.

Furthermore, by providing first and second pairs of flow rate sensors 80a, 80b, a control check is provided, in that the control system can monitor the output of each of the pairs of flow rate sensors 80a, 80b, and, if the measured output exceeds a predetermined threshold, raise an alert and/or shut down the vaporizer.

In this embodiment the flow path 79 includes a stub path 81, and the fresh gas sensing unit 7 further comprises at least one fresh gas characteristic sensor 83 in the stub path 81.

In this embodiment the stub path 81 is downstream of the at least one flow rate sensor 80a, 80b.

In an alternative embodiment the stub path 81 could be upstream of the at least one flow rate sensor 80a, 80b.

In this embodiment the stub path 81 is located in a substantially linear section of the flow path 79.

In this embodiment the stub path 81 comprises a sensor cavity 85 at which the at least one fresh gas characteristic sensor 83 is located, and a flow restriction 87 which fluidly connects the flow path 79 to the sensor cavity 85.

In this embodiment the at least one fresh gas characteristic sensor 83 is a mass flow rate sensor, here a mass flow sensor.

In this embodiment the at least one fresh gas characteristic sensor 83 is of the same kind as the flow rate sensors 80a, 80b.

In this embodiment the flow restriction 87 comprises a flow channel of smaller diameter than the flow path 79, here of a diameter of 1.75 mm. In preferred embodiments the flow restriction has an area of about 1.5 mm$^2$ to about 3.5 mm$^2$, preferably about 2 mm$^2$ to about 3 mm$^2$.

With this configuration, the flow restriction 87 provides for an extended residence time of the fresh gas in the sensor cavity 85, which in effect provides that the at least one fresh gas characteristic sensor 83 provides for a "zero flow" or "static" measurement of a characteristic of the gas flow which is representative of composition. In this embodiment the average residence time in the sensor cavity 85 is at least 20 seconds, optionally at least 25 seconds, optionally at least 30 seconds, and optionally at most 60 seconds. In this embodiment the average residence time in the sensor cavity 85 is at most 60 seconds, optionally at most 40 seconds, and optionally at most 35 seconds. The present inventors have established that this "zero flow" or "static" measurement of the fresh gas flow enables a more precise determination of the flow rate of the fresh gas flow when the measurement from the at least one fresh gas characteristic sensor 83 is used to provide a compensation factor for the flow rate of the fresh gas flow as measured by the flow rate sensors 80a, 80b.

In this embodiment the measurement from the at least one fresh gas characteristic sensor 83 provides a compensation factor, and, for this compensation factor, a look-up table is selected, from which a compensated flow rate is determined.

In an alternative embodiment the compensation factor can be applied to a fitted function for a flow rate as measured by the flow rate sensors 80a, 80b.

In a further embodiment the measurement from the at least one fresh gas characteristic sensor 83 provides a compensation factor, and, for this compensation factor, a look-up table is selected, from which a compensated flow rate is determined and applied to a fitted function for a flow rate as measured by the flow rate sensors 80a, 80b.

In this embodiment the fresh gas sensing unit 7 includes a vaporized medium inlet port 89 in the flow path 79 thereof and downstream of the at least one fresh gas characteristic sensor 83, which is fluidly connected to the outlet port 97 of the vaporized medium sensing unit 9, by which the vaporized medium is metered into the flow of fresh gas.

In one alternative embodiment, as illustrated in FIG. 7, the flow restriction 87 could comprise a porous element 91, here a sintered element, which is located in the stub path 81.

In this embodiment, as particularly illustrated in FIGS. 8(a) to (d), the vaporized medium sensing unit 9 comprises a body 92 which includes a flow channel 93 which includes an inlet port 95 which is fluidly connected to the outlet port 76 of the metering valve 72 and an outlet port 97 through which a flow of the vaporized medium is delivered, and at least one flow sensor 101 for detecting a flow rate of the vaporized medium through the flow channel 93.

In this embodiment the body 92 comprises first and second body parts 103a, b and an annular seal 105 which surrounds the flow channel 93.

In this embodiment at least one of the first and second body parts 103a, b of the body 92 is formed of a material of high thermal conductivity.

In one embodiment at least one of the first and second body parts 103a, b of the body 92 is formed of the same material as the tank 21 of the reservoir unit 5.

In this embodiment the at least one of the first and second body parts 103a, b of the body 92 is thermally connected, here fixed directly, to the tank 21 of the reservoir unit 5. With this configuration, the body 92 is maintained in a heated state, which prevents condensation in the flow channel 93, which could hinder accurate detection of the flow rate of the vaporized medium.

In this embodiment the flow channel 93 is a linear channel.

In this embodiment the flow channel 93 has a cross-sectional area of 2 mm$^2$, and in preferred embodiments has a cross-sectional area from about 1.5 mm$^2$ to about 2.5 mm$^2$. This configuration has been found to provide for establishment of a laminar flow over the at least one flow sensor 101 for a broad range of flows.

In this embodiment the at least one flow sensor 101 is a mass flow rate sensor, here a mass flow sensor.

In this embodiment the vaporized medium sensing unit 9 includes first and second flow sensors 101a, b. By providing first and second flow sensors 101a, b, a control check is provided, in that the control system can monitor the output of each of the flow sensors 101a, b, and, if the measured output exceeds a predetermined threshold, raise an alert and/or shut down the vaporizer.

In this embodiment the manifold 10 comprises a thermal block 111 of a material of high thermal conductivity which includes flow passages for the vaporized medium. By being thermally connected to the tank 21 of the reservoir unit 5, which is heated by the heater 23, the manifold 10 is maintained in a heated state, which prevents condensation of the vaporized medium in the flow passages.

In one embodiment the thermal block 111 is formed of the same material as the tank 21 of the reservoir unit 5.

In this embodiment the manifold 10 includes a connector 115 which fluidly connects the outlet port 97 of the vaporized medium sensing unit 9, here through a flow passage in the thermal block 111, to vaporized medium inlet port 89 in the flow path 79 of the fresh gas sensing unit 7.

In one embodiment the connector 115 is formed of the same material as the tank 21 of the reservoir unit 5.

Finally, it will be understood that the present invention has been described in its preferred embodiments and can be modified in many different ways without departing from the scope of the invention as defined in the appended claims.

For example, although the present invention has been described with reference to the delivery of a general anaesthetic, it will be understood that the present invention has application to the vaporization of any medium for delivery in a gas flow.

The invention claimed is:

1. A vaporizer for delivery of a volatile medium to a gas flow, the vaporizer comprising:
- a gas delivery which receives a first flow of gas and provides a second flow of gas containing a metered amount of a vaporized medium;
- a reservoir which contains a volatile medium and maintains a supply of the vaporized medium, wherein the reservoir comprises:
  - a tank which contains the volatile medium in liquid form,
  - a heater which heats the volatile medium to a vaporization temperature in order to vaporize the volatile medium and maintain the vaporized medium at an operating pressure in a headspace of the tank, and
  - a metering valve by which the vaporized medium is metered from the tank into the first gas flow,
  - wherein the tank has a thermal mass which is sufficient to maintain the contained volatile medium at the vaporization temperature for at least 3 minutes following de-actuation of the heater;
- a gas sensor which senses a flow rate and/or composition of the first gas flow;
- a vaporized medium sensor which senses a flow rate of the vaporized medium into the first gas flow;
- a manifold which includes flow paths for the vaporized medium and fluidly connects the reservoir and the vaporized medium sensor; and
- a controller which controls a flow rate of the first gas flow and an amount of the vaporized medium which is metered by the metering valve from the tank into the first gas flow to provide the second gas flow.

2. The vaporizer of claim 1, wherein the gas delivery comprises an inlet which is connected to a supply of gas and an outlet which provides the second flow of gas containing a metered amount of the vaporized medium.

3. The vaporizer of claim 1, wherein the tank has a thermal mass which is sufficient to maintain the contained volatile medium at the vaporization temperature for at least 5 minutes following de-actuation of the heater.

4. The vaporizer of claim 1, wherein the gas sensor comprises a gas inlet port through which the first gas flow is delivered, an outlet port from which the second gas flow is delivered, a flow path which fluidly connects the gas inlet port and the outlet port, and at least one flow rate sensor which senses the flow rate of the first gas flow.

5. The vaporizer of claim 4, wherein the flow path includes a stub path, and the gas sensor further comprises at least one gas characteristic sensor in the stub path which measures a characteristic of the first gas flow which is representative of the composition of the first gas flow, with the measurement from the gas characteristic sensor being used to provide a compensation factor for the flow rate of the first gas flow as measured by the at least one flow rate sensor.

6. The vaporizer of claim 5, wherein the gas sensor includes a vaporized medium inlet port in the tub flow path thereof and downstream of the at least one gas characteristic sensor, which is fluidly connected to the vaporized medium sensor.

7. The vaporizer of claim 1, wherein the tank is configured to maintain the contained volatile medium at the vaporization temperature while delivering the vaporized medium at a flow rate of at least 1 L/min.

8. A vaporizer for delivery of a volatile medium to a gas flow, the vaporizer comprising:
- a gas delivery which receives a first flow of gas and provides a second flow of gas containing a metered amount of a vaporized medium;
- a reservoir which contains a volatile medium and maintains a supply of the vaporized medium, wherein the reservoir comprises:
  - a tank which contains the volatile medium in liquid form,
  - a heater which heats the volatile medium to a vaporization temperature in order to vaporize the volatile medium and maintain the vaporized medium at an operating pressure in a headspace of the tank,
  - a metering valve by which the vaporized medium is metered from the tank into the first gas flow, and
- a filler assembly by which volatile medium is introduced into the tank, wherein the filler assembly comprises:
  - a body which includes a port for receiving a filling container,
  - a chamber which is fluidly connected to the tank, and
  - a filling valve which, when opened, opens a fluid connection between the port and the chamber so as to provide for filling of the tank with volatile medium from the filling container, wherein the filling valve comprises:
- a bore which sealingly receives an external nozzle of the filling container and includes at least one valve opening,
- a seat which receives a valve element of the filling container which is internal to the nozzle and when depressed opens a fluid connection between the nozzle and a body of the filling container, and
- a valve element which is normally biased to close the at least one valve opening and engaged by the nozzle of the filling container to displace the valve element of the filling valve and open the at least one valve opening, and the valve element of the filling valve includes at least one projection which projects through the at least one valve opening and is engaged by the nozzle of the filling container to displace the valve element of the filling valve;

a gas sensor which senses a flow rate and/or composition of the first gas flow;

a vaporized medium sensor which senses a flow rate of the vaporized medium into the first gas flow;

a manifold which includes flow paths for the vaporized medium and fluidly connects the reservoir and the vaporized medium sensor; and a controller which controls a flow rate of the first gas flow and an amount of the vaporized medium which is metered by the metering valve from the tank into the first gas flow to provide the second gas flow.

9. The vaporizer of claim 8, wherein the seat extends proximally of the at least one projection of the valve element of the filling valve.

10. The vaporizer of claim 8, wherein the filling value comprises a shut-off valve which is operable to prevent delivery of the vaporized medium into the first gas flow.

11. A vaporizer for delivery of a volatile medium to a gas flow, the vaporizer comprising:
- a gas delivery which receives a first flow of gas and provides a second flow of gas containing a metered amount of a vaporized medium;
- a reservoir which contains a volatile medium and maintains a supply of the vaporized medium, wherein the reservoir comprises:
  - a tank which contains the volatile medium in liquid form,
  - a heater which heats the volatile medium to a vaporization temperature in order to vaporize the volatile medium and maintain the vaporized medium at an operating pressure in a headspace of the tank,
  - a metering valve by which the vaporized medium is metered from the tank into the first as flow, and
  - a filler assembly by which volatile medium is introduced into the tank, wherein the filler assembly comprises:
    - a body which includes a port for receiving a filling container,
    - a chamber which is fluidly connected to the tank,
    - a filling valve which, when opened, opens a fluid connection between the port and the chamber so as to provide for filling of the tank with volatile medium from the filling container, and
    - a loader/unloader which engages the filling container and loads/unloads the filling container to the filling valve, wherein the loader/unloader comprises:
      - an engagement member which is adapted to engage the filling container when the filling container is inserted into the port of the body,
      - a lever assembly which is coupled to the engagement member and operative between a first, unlocked position and a second, locked position in which the filling valve is open to allow for filling of the tank by the filling container, the engagement member including a slide element which is movable laterally and acts to engage the filling container to lock the filling container to the engagement member when the lever assembly is in the locked position, the slide element comprising at least one slide part which is slideably rotated about at least one pivot, and
      - a guide member which acts to cause the at least one slide part to slide laterally when the loader/unloader is moved axially between the unlocked and locked positions;

a gas sensor which senses a flow rate and/or composition of the first gas flow;

a vaporized medium sensor which senses a flow rate of the vaporized medium into the first gas flow;

a manifold which includes flow paths for the vaporized medium and fluidly connects the reservoir and the vaporized medium sensor; and a controller which controls a flow rate of the first gas flow and an amount of the vaporized medium which is metered by the metering valve from the tank into the first gas flow to provide the second gas flow.

12. The vaporizer of claim 11, wherein the lever assembly comprises a lever which is pivotally coupled to the body of the filler assembly, and a coupling which couples the lever to the engagement member.

13. The vaporizer of claim 12, wherein the slide element comprises first and second slide parts which are rotated about first and second pivots, and the guide member includes first and second guides which receive the projections of the slide part.

14. The vaporizer of claim 12, wherein the filling valve comprises:
- a bore which sealingly receives an external nozzle of the filling container and includes at least one valve opening,
- a seat which receives a valve element of the filling container which is internal to the nozzle and when depressed opens a fluid connection between the nozzle and a body of the filling container, and
- a valve element which is normally biased to close the at least one valve opening and engaged by the nozzle of the filling container to displace the valve element of the filling valve and open the at least one valve opening, and, on moving the lever assembly to the locked position, the engagement member is moved in relation to the body of the filler assembly, which causes the valve element of the filling container to engage the seat of the filling valve and the nozzle of the filling container to engage the valve element of the filling valve, which causes the valve element of the filling container and the valve element of the filling valve to be opened.

15. The vaporizer of claim 14, wherein the nozzle of the filling container engages the valve element of the filling valve ahead of the valve element of the filling container engaging the seat of the filling valve, such that the valve element of the filling valve is opened ahead of the valve element of the filling container.

16. The vaporizer of claim 12, wherein the slide element includes a recess or projection, which, when the engagement member is moved to the locked position, is located at a detent to prevent sliding of the slide element.

17. The vaporizer of claim 16, wherein the recess or projection and the detent are configured such that the slide element is moved to an open position when the lever assembly is moved to the unlocked position.

18. The vaporizer of claim 17, wherein the lever assembly is configured to be movable from the unlocked position to a release position by movement of the lever assembly in a sense opposite to that in which the lever assembly is moved to the locked position, and the recess or projection and the detent are configured such that the slide element is moved to an open position when the lever assembly is in the release position.

19. The vaporizer of claim 11, wherein the at least one slide part includes a projection, and the guide member includes at least one guide which receives the projection of the at least one slide part.

20. The vaporizer of claim 19, wherein the slide element comprises first and second slide parts which are rotated about first and second pivots, and the guide member includes first and second guides which receive the projections of the slide parts.

21. The vaporizer of claim 19, wherein the at least one guide includes a first guide section, in which the projection of the at least one slide part is located when the loader/unloader is in the unlocked position, and a second guide section which is disposed laterally inwardly of the first guide section, in which the projection of the at least one slide part is located when the loader/unloader is in the locked position, whereby, when the loader/unloader is in the unlocked position, the projection of the at least one slide part is located in the first guide section of the at least one guide and the at least one slide part has a first, laterally-outward position which allows the filling container to be inserted into the bore of the filling valve, and, when the loader/unloader is moved to the locked position, the projection of the at least one slide part is located in the second guide section of the at least one guide and the at least one slide part has a second, laterally-inward position in which the filling container is engaged by the at least one slide part and prevents release of the filling container.

22. A vaporizer for delivery of a volatile medium to a as flow, the vaporizer comprising:
- a gas delivery which receives a first flow of gas and provides a second flow of gas containing a metered amount of a vaporized medium;
- a reservoir which contains a volatile medium and maintains a supply of the vaporized medium, wherein the reservoir comprises:
  - a tank which contains the volatile medium in liquid form,
  - a heater which heats the volatile medium to a vaporization temperature in order to vaporize the volatile medium and maintain the vaporized medium at an operating pressure in a headspace of the tank, and
  - a metering valve by which the vaporized medium is metered from the tank into the first gas flow;
- a gas sensor which senses a flow rate and/or composition of the first gas flow;
- a vaporized medium sensor which senses a flow rate of the vaporized medium into the first gas flow, wherein the vaporized sensor comprises:
  - a body which includes a flow channel which includes an inlet port which is fluidly connected to the reservoir and an outlet port which is fluidly connected to the gas delivery, and
  - at least one flow sensor which detects a flow rate of the vaporized medium through the flow channel,
- wherein the body of the vaporized medium sensor is thermally connected to the reservoir;
- a manifold which includes flow paths for the vaporized medium and fluidly connects the reservoir and the vaporized medium sensor; and
- a controller which controls a flow rate of the first gas flow and an amount of the vaporized medium which is metered by the metering valve from the tank into the first gas flow to provide the second gas flow.

23. The vaporizer of claim 22, wherein the flow channel of the vaporized medium sensor is a linear channel having a cross-sectional area of from about 1.5 $mm^2$ to about 2.5 $mm^2$.

* * * * *